US008685721B2

(12) United States Patent
Sung et al.

(10) Patent No.: US 8,685,721 B2
(45) Date of Patent: *Apr. 1, 2014

(54) STABLE CONSTITUTIVELY HIGH EXPRESSION VECTOR FOR PREPARING HPV VACCINE AND RECOMBINANT LACTIC ACID BACTERIA TRANSFORMED THEREBY

(75) Inventors: Moon-Hee Sung, Daejeon (KR); Haryoung Poo, Daejeon (KR); Il Han Lee, Daejeon (KR)

(73) Assignees: Bioleaders Corporation, Daejeon (KR); Kookmin University Industry-Academy Cooperation Foundation, Seoul (KR)

( * ) Notice: Subject to any disclaimer, the term of this patent is extended or adjusted under 35 U.S.C. 154(b) by 49 days.

This patent is subject to a terminal disclaimer.

(21) Appl. No.: 13/143,700

(22) PCT Filed: Jan. 8, 2010

(86) PCT No.: PCT/KR2010/000126
§ 371 (c)(1),
(2), (4) Date: Sep. 7, 2011

(87) PCT Pub. No.: WO2010/079991
PCT Pub. Date: Jul. 15, 2010

(65) Prior Publication Data
US 2011/0318384 A1    Dec. 29, 2011

(30) Foreign Application Priority Data

Jan. 8, 2009    (KR) ........................ 10-2009-0001510

(51) Int. Cl.
*C12N 15/37*    (2006.01)
*A61K 39/12*    (2006.01)
*A61K 39/07*    (2006.01)
*A61K 39/09*    (2006.01)

(52) U.S. Cl.
USPC .................. 435/320.1; 424/201.1; 424/204.1; 424/246.1; 424/93.45

(58) Field of Classification Search
None
See application file for complete search history.

(56) References Cited

U.S. PATENT DOCUMENTS

| 6,783,763 | B1 | 8/2004 | Choppin et al. |
| 7,288,258 | B2 | 10/2007 | Choppin et al. |
| 7,425,438 | B2 | 9/2008 | Sung et al. |
| 7,553,636 | B2 | 6/2009 | Sung et al. |
| 2004/0253704 | A1 | 12/2004 | Sung et al. |
| 2005/0033025 | A1 | 2/2005 | Choppin et al. |
| 2005/0249752 | A1 | 11/2005 | Sung et al. |
| 2008/0248044 | A1 | 10/2008 | Choppin et al. |
| 2009/0117151 | A1 | 5/2009 | Sung et al. |
| 2010/0196956 | A1 | 8/2010 | Sung et al. |

FOREIGN PATENT DOCUMENTS

| KR | 10-0366608 B1 | 1/2003 |
| KR | 10-0469800 B1 | 2/2005 |
| KR | 10-0609866 B1 | 8/2006 |
| KR | 10-2008-0086161 A | 9/2008 |
| KR | 10-0872042 B1 | 12/2008 |
| WO | WO2008/115019 A1 * | 9/2008 |

OTHER PUBLICATIONS

Poo H et al. Oral administration of human papillomavirus type 16 E7 displayed on *Lactobacillus casei* induces E7-specific antitumor effects in C57/BL6 mice. Int J Cancer. Oct. 1, 2006;119(7):1702-9.*
GenBank: AAP60031.1, pbublished Apr. 2, 2004.*
French et al. J. Mol. Evol., 1983, 19:171-175.*
J. T. Barret, "Textbook of Immunology", 1983.
L. Gao et al., "Immune response to human papillomavirus type 16 E6 gene in a live vaccinia vector", Journal of General Virology, 1994, pp. 157-164, vol. 75.
Yasuo Kawasaki et al., "Binding of RepE Initiator Protein to Mini-F DNA Origin (ori2)", The Journal of Biological Chemistry, 1992, pp. 11520-11524, vol. 267, No. 16.
Douglas R. Lowy et al., "Genital human papillomavirus infection", Proc. Natl. Acad. Sci, USA, 1994, pp. 2436-2440, vol. 91.
G. Meneguzzi et al., "Immunization against Human Papillomavirus Type 16 Tumor Cells with Recombinant Vaccinia Viruses Expressing E6 and E7", Virology, 1991, pp. 62-69, vol. 181.
Tomio Morino et al., "Construction of a runaway vector and its use for a high-level expression of a cloned human superoxide dismutase gene", Appl. Microbiol. Biotechnol., 1988, pp. 170-175, vol. 28.
D. Nardelli-Haefliger et al., "Human Papillomavirus Type 16 Virus-Like Particles Expressed in Attenuated *Salmonella typhimurium* Elicit Mucosal and Systemic Neutralizing Antibodies in Mice", Infection and Immunity, 1997, pp. 3328-3336, vol. 65, No. 8.
P. Pisani et al., "Estimates of the Worldwide Mortality from Eighteen Major Cancers in 1985. Implications for Prevention and Projections of Future Burden", Int. J. Cancer, 1993. pp. 891-903, vol. 55.

(Continued)

*Primary Examiner* — Stacy B. Chen
*Assistant Examiner* — Nick Zou
(74) *Attorney, Agent, or Firm* — Rabin & Berdo, P.C.

(57) ABSTRACT

A surface expression vector for preparing HPV immunogenic compositions, in which the surface expression vector contains a gene encoding a repE mutant protein having an amino acid sequence of SEQ ID NO: 1, a promoter, a poly-gamma-glutamate synthetase complex gene, and a gene which is linked with the poly-gamma-glutamate synthetase complex gene and encodes a tumor induction-associated antigen protein of human papillomavirus.
An expression vector constitutively expressing a high level of the human papillomavirus (HPV) antigen protein is provided. Also, a recombinant lactic acid bacteria, transformed with the expression vector and expressing the HPV antigen protein on the surface thereof, and a composition comprising the recombinant lactic acid bacteria are provided. The recombinant lactic acid bacteria and the composition are very effective as a immunogenic composition for the treatment of cervical cancer, because they can be applied orally or directly to the vagina.

9 Claims, 11 Drawing Sheets

(56) References Cited

OTHER PUBLICATIONS

H. Poo et al., "Oral administration of human papillomavirus type 16 E7 displayed on *Lactobacillus casei* induces E7-specific antitumor effects in C57/BL6 mice", Int. J. Cancer, 2006, pp. 1702-1709, vol. 119.

M. Smahel et al., "Modified HPV16 E7 Genes as DNA Vaccine against E7-Containing Oncogenic Cells", Virology, 2001, pp. 231-238, vol. 281.

Y. Thanavala et al., "Immunogenicity of transgenic plant-derived hepatitis B surface antigen", Proc. Natl. Acad. Sci. USA, 1995, pp. 3358-3361, vol. 92.

M. E. Ressing et al., "Human CTL Epitopes Encoded by Human Papillomavirus Type-16 E6 and E7 Identified Through in-vivo and in-vitro Immunogenicity Studies of HLA-A*0201-Binding Peptides", Journal of Immunology, 1995, pp. 5934-5943, vol. 154, No. 11.

English Language Abstract of KR 10-2001-0044019 A which is application publication of KR 10-0366608 B1.

English Language Abstract of KR 10-2004-0032824 A which is application publication of KR 10-0469800 B1.

English Language Abstract of KR 10-2004-0034511 A which is application publication of KR 10-0609866 B1.

English Language Abstract of KR 10-2007-0031248 A which is application publication of KR 10-0872042 B1.

English Language Abstract of KR 10-2008-0086161 A.

International Search Report of PCT/KR2010/000126 mailed on Sep. 27, 2010.

\* cited by examiner

A.

B.

STABLE CONSTITUTIVELY HIGH EXPRESSION VECTOR FOR PREPARING HPV VACCINE AND RECOMBINANT LACTIC ACID BACTERIA TRANSFORMED THEREBY

TECHNICAL FIELD

The present invention relates to a surface expression vector for preparing HPV therapeutic vaccines, in which the surface expression vector contains a gene encoding a repE mutant protein having an amino acid sequence of SEQ ID NO: 1, a promoter, a poly-gamma-glutamate synthetase complex gene, and a gene which is linked with the poly-gamma-glutamate synthetase complex gene and encodes a tumor induction-associated antigen protein of human papillomavirus.

BACKGROUND ART

It is known that the production of useful foreign proteins in attempts to express large amounts of the foreign proteins depends on the copy number of genes, that is, the number of plasmids, and the strength of promoters which are used to control transcription. It was reported that the expression of target proteins can be increased by changing the number of plasmid vectors in individual bacteria, in addition to high-expression promoters which are conventionally frequently used (Tomio, M. et al., *Appl. Microbiol. Biotechnol.*, 28: 170, 1988). Also, it was reported that RepE mutations in the mini-F plasmid can change the number of 25 plasmids in individual bacteria (Yasuo, K. et al., *J. Biol. Chem.*, 267:11520, 1992).

Human papillomavirus (HPV) is estimated to infect more than 50% of adults worldwide. Particularly, four types of HPV including HPV 16, 18, 31 and 45 were reported to cause more than 80% of cervical cancer cases (Lowy, D. R. et al., *Proc. Nat. Acad. Sci.*, 91: 2436, 1994).

Cervical cancer is the second most common cancer in women next to breast cancer, and according to WHO (World Health Organization), it is estimated that more than 500,000 new cervical cancer cases worldwide each year occur and more than 300,000 patients worldwide each year die from cervical cancer. Especially in developing countries, cervical cancer is a leading cause of death in women (Pisani, P. et al., *Int. J. Cancer*, 55: 891, 1993). The IARC report showed that the number of chronic HPV infection patients in developing countries is significantly larger than in advanced countries and that the most effective way to eradicate HPV infection is to administer HPV prophylactic vaccines.

The development of vaccines associated with cervical cancer has been focused on two types of prophylactic vaccines and therapeutic vaccines. The prophylactic vaccines aim to produce a stronger neutralizing antibody by HPV L1/L2 antigen, thus preventing a host from HPV infection, and preventing the disease from further progression, even if already infected. On the other hand, the therapeutic vaccine targets HPV E6/E7 and aims to induce specific cellular immune responses to degenerate formed lesions or malignant tumors.

Because the HPV E6/E7 protein is a cancer-specific antigen associated with the carcinogenesis of HPV-infected cells, studies on the use of the E6/E7 protein as a target for immune therapy of cervical cancer have been continued. Indeed, there is a report that when a HPV E6/E7 protein synthesized in a microbial system was administered to mice injected with tumor cells, tumor formation was inhibited or delayed (Gao, L. et al., *J. Gen. Viol.*, 75: 157, 1994, Meneguzzi, G. et al., *Virology*, 181: 62, 1991). However, in the case in which live viral vaccines are used, problems associated with excessive viral replication can arise, similar to other cases. Thus, live virus vaccines are used only for research purposes in many cases and have disadvantages in that they take a long period of time to be commercialized and need considerable clinical trials.

Meanwhile, studies on the development of vaccines including bacterial vectors are also being actively conducted, and there is a report that HPV 16 VLP synthesized in attenuated *Salmonella typhimurium* induces the production of antigen-specific antibodies in the mucosa or whole body of mice (Denis, N. et al., *Infection and immunity*, 65: 3328, 1997). In the case of vaccines composed of synthetic peptides, only epitopes required to induce immune responses are synthesized for vaccination, and epitopes causing cytotoxic T lymphocyte (CTL) responses to HPV 16 E6/E7 have already been elucidated (Ressing, M. E. et al., *J. Immunol.*, 154: 5934, 1995).

In addition to such attempts, studies on using transgenic vegetables themselves (obtained from vegetables including tomato and potato) as oral vaccines or edible vaccines to produce viral antigens in plants are being conducted. Typical examples thereof include hepatitis B surface antigen particles (Thavala, Y. F. and Artzen, C. J., *Pro. Natl. Acad. Sci. USA*, 92: 3358, 1995) and the capsid proteins L1 and L2 of papillomavirus (Korean Patent Registration No. 0366608). However, the plant systems have a problem in that the commercial use thereof is limited, because the amount of HPV L1 protein expressed is small and problems associated with purification occur.

Thus, in view of the fact that HPV-infected population is mainly concentrated on developing countries, the development of a method of preparing HPV antigens in a more economical and stable manner is urgently required in order to prevent and treat tumors derived from papillomavirus in the skin mucosa of oral cavities or genital organs.

The present inventors previously developed a vector for effectively expressing an HPV antigen protein on the surface of transformed recombinant microorganisms and a method for expressing an HPV antigen protein on the surface of the microorganisms (Korean Patent Registration No. 0609866).

Accordingly, the present inventors have made extensive efforts to develop a vector capable of more stably and constitutively expressing a high level of an HPV antigen protein on the surface of transformed recombinant lactic acid bacteria and, as a result, have found that the HPV antigen protein is more stably expressed at a high level in recombinant microorganisms transformed with a vector containing a repE mutant gene, thereby completing the present invention.

DISCLOSURE OF INVENTION

It is a main object of the present invention to provide a vector capable of stably and constitutively expressing a high level of an HPV antigen protein on the surface of transformed recombinant lactic acid bacteria using a repE mutant gene.

Another object of the present invention is to provide recombinant lactic acid bacteria transformed with said expression vector and a method for preparing the HPV antigen protein using said lactic acid bacteria.

Still another object of the present invention is to provide a vaccine for treating cervical cancer, which comprises said transformed recombinant lactic acid bacteria.

To achieve the above objects, the present invention provides a surface expression vector containing: a repE mutant gene having an amino acid sequence of SEQ ID NO: 1; a promoter; a poly-gamma-glutamate synthetase complex gene; and a gene which is linked with the poly-gammaglutamate synthetase complex gene and encodes a tumor induction-associated antigen protein of human papillomavirus.

The present invention also provides a recombinant microorganism transformed with said vector.

The present invention also provides a vaccine for treating cervical cancer, which contains, as an active ingredient, a recombinant microorganism having an HPV antigen protein expressed on the surface thereof.

The present invention also provides a method for preparing a microorganism having an HPV antigen expressed on the surface thereof, the method comprising the steps of: culturing a recombinant microorganism transformed with said vector to express an HPV antigen on the surface of the microorganism; and collecting the recombinant microorganism having the HPV antigen expressed on the surface thereof.

The present invention also provides a vaccine for treating cervical cancer, which contains, as an active ingredient, the microorganism prepared by said method and having an HPV antigen expressed on the surface thereof.

BEST MODE FOR CARRYING OUT THE INVENTION

Figure 1:
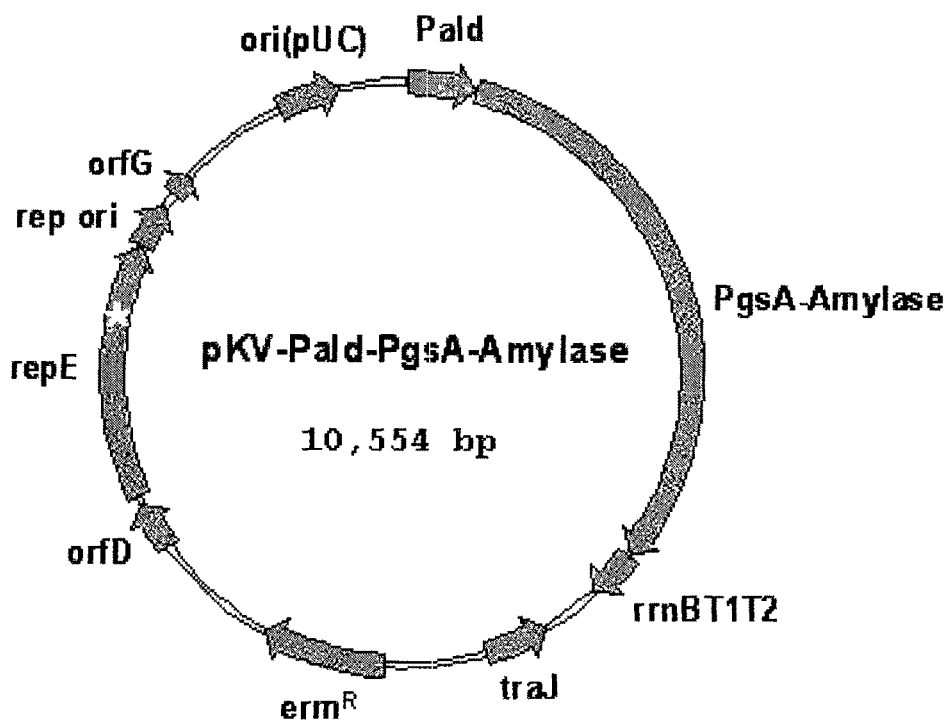
FIG. 1 shows a cleavage map of a pKV-Pald-PgsA-Amylase vector introduced with a repE mutant gene.

In one aspect, the present invention is directed to a surface expression vector containing: a repE mutant gene having an amino acid sequence of SEQ ID NO: 1; a promoter; a poly-gamma-glutamate synthetase complex gene; and a gene which is linked with the poly-gamma-glutamate synthetase complex gene and encodes a tumor induction-associated antigen protein of human papillomavirus.

In the present invention, a repE mutant gene having an amino acid sequence of SEQ ID NO: 1, which can be stably maintained in transformed microorganisms, was introduced into the transformed microorganisms together with an aldolase promoter (Pald) derived from the aldolase gene of *Lactobacillus casei*. As a result, it was seen that the expression of a target protein in the microorganisms was increased. In order to confirm that a shuttle vector of the present invention is stably maintained in the recombinant microorganisms and that a target protein is expressed in the recombinant microorganisms, an amylase gene as a target gene was introduced into the recombinant microorganisms, and the expression of amylase in the recombinant microorganisms was analyzed.

In addition, for surface expression of a target protein, a poly-gamma-glutamate synthetase complex gene that is a surface anchoring motif was located such that it was expressed in a state linked with a target protein. Herein, the poly-gamma-glutamate synthetase complex gene is preferably pgsBCA, and more preferably pgsA (Korean Patent Registration No. 469800).

In one embodiment of the present invention, an HPV16 E7-encoding gene was fused with pgsA such that the HPV16 E7 protein as a target protein was fused with the C-terminal end of PgsA, thereby preparing a pKV-Pald-PgsA-E7 vector capable of constitutively expressing an HPV antigen protein on the surface of lactic acid bacteria. Also, the expression vector was inserted into *Lactobacillus casei*, thus preparing transformed recombinant lactic acid bacteria expressing the HPV antigen protein.

As used herein, the term "target protein" or "foreign protein" refers to a protein which cannot be normally found in transformed host cells expressing the protein. For example, when manipulation is performed such that a virus-derived or tumor-derived protein is artificially expressed in lactic acid bacteria, the protein is referred to as a foreign protein or a target protein.

In another aspect, the present invention is also directed to a recombinant microorganism transformed with said vector, the recombinant microorganism expressing an HPV antigen protein on the surface thereof, and a vaccine for treating cervical cancer, which contains, as an active ingredient, the transformed recombinant microorganism.

As used herein, the term "hosts" or "microorganisms" refers to lactic acid bacteria that are probiotic gram-positive bacteria, and common criteria used for selecting probiotic microorganisms include the following: (i) a microorganism derived from human; (ii) stability against bile, acid, enzyme and oxygen; (iii) ability to adhere to intestinal mucosa; (iv) colonization potential in the human gastrointestinal tract; (v) production of antimicrobial substances; and (vi) demonstrable efficacy and safety. On the basis of such criteria, it is apparent that lactic acid bacteria are friendly and harmless to the human body. Thus, when transformants which use lactic acid bacteria as hosts are applied to the human body in order to deliver a gene or protein for preventing or treating disease, a step of detoxifying bacterial strains is not required, unlike a conventional method for preparing vaccines which uses bacterial strains.

In the present invention, the lactic acid bacteria which are used as hosts include *Lactobacillus* sp., *Streptococcus* sp. and *Bifidobacterium* sp. Typically, said *Lactobacillus* sp. includes *L. acidophilus, L. casei, L. plantarum, L. ferementum, L. delbrueckii, L. johnsonii* LJI, *L. reuteri* and *L. bulgaricus*, said *Streptococcus* sp. includes *S. thermophiles*, and *Bifidobacterium* sp. includes *B. infantis, B. bijidum, B. longum, B. psuedolongum, B. breve, B. lactis* Bb-12 and *B. adolescentis*. Preferably, *Lactobacillus* sp. is used as a host.

In still another aspect, the present invention is directed to a method for preparing a microorganism having an HPV antigen expressed on the surface thereof, the method comprising the steps of: culturing a recombinant microorganism transformed with said vector to express an HPV antigen on the surface of the microorganism; and collecting the recombinant microorganism having the HPV antigen expressed on the surface thereof.

The culture of the recombinant microorganisms according to the present invention may be carried out according to a method well known in the art, and culture conditions, including culture temperature and time and the pH of medium can be suitably controlled. The collection of recombinant microbial cells from the culture broth can be carried out using conventional isolation techniques, for example, centrifugation or filtration.

In yet another aspect, the present invention is directed to a vaccine for treating cervical cancer, which contains, as an active ingredient, the microorganism prepared by said method and having an HPV antigen expressed on the surface thereof.

In addition, the present invention is directed to a vaccine for treating cervical cancer, which is oral.

Vaccines are drugs that use live organisms for preventive purposes against diseases to stimulate the immune system. Immune activation refers to a process of effectively removing antigens by production of antibodies in organisms, stimulation of T-lymphocytes or stimulation of other immune cells (e.g., macrophages). A detailed overview of immunology relating to such details is easily understood by those skilled in the art (Barrett, J. T., Textbook of Immunology, 1983). A transformed microorganism vaccine expressing a target protein as an antigen may be administered to mammals, and preferably humans.

The preparation of the vaccine composition can be carried out using standard techniques. A dose suitable for administration varies depending on the antigenicity of gene products and may be an amount in which the vaccine can sufficiently induce typical immune responses. The dose can be easily determined through usual experimental procedures. The typical initial dose of the vaccine is 0.001-1 mg antigen/kg of weight. If necessary, the dose can be increased so as to offer a preferred level of protection, or the vaccine is used in a multiple dose. The dose can be determined by those skilled in the art and can vary depending on formulation method, administration type, patient's age, body weight, sex, severity of disease, diet, administration frequency, administration route, excretion rate and response sensitivity.

The most preferred embodiment of the inventive surface expression vector for preparing an HPV vaccine encoding the HPV antigen protein E7 is a surface expression vector containing: a gene encoding a repE mutant protein having an amino acid sequence of SEQ ID NO: 1; a lactic acid bacteria-derived aldolase promoter; a poly-gamma-glutamate synthetase complex gene selected from the group consisting of pgsB, pgsC and pgsA for surface expression; and a gene which encodes the tumor induction-associated antigen protein E7 of human papillomavirus and is linked with the poly-gamma-glutamate synthetase complex gene. Recombinant lactic acid bacteria transformed with the vector may be cultured to express the HPV antigen protein E7 on the surface thereof, and then used directly as a vaccine.

The most preferred embodiment of the inventive surface expression vector for preparing an HPV vaccine encoding the HPV antigen protein E7(Rb) is a surface expression vector containing: a gene encoding repE mutant protein having an amino acid sequence of SEQ ID NO: 1; a lactic acid bacteria-derived aldolase promoter; a poly-gamma-glutamate synthetase complex gene selected from the group consisting of pgsB, pgsC and pgsA for surface expression; and a gene which encodes the tumor induction-associated antigen protein E7(Rb) of human papillomavirus and is linked with the poly-gamma-glutamate synthetase complex gene. Recombinant lactic acid bacteria transformed with the vector may be cultured to express the HPV antigen protein E7(Rb) on the surface thereof, and then used directly as a vaccine.

In order for the vaccine to be effective in producing an antibody, an antigenic substance must be released in vivo, such that the antibody-producing mechanism of vaccinated individuals can come into play. Thus, a microbial carrier of a gene product must be preferentially introduced in vivo for immune responses. In order to stimulate a preferred response by an antigen which is presented in the transformed recombinant lactic acid bacteria of the present invention, the vaccine is preferably administered orally or directly to the uterine cervix in the form of a spray.

For oral administration of the vaccine composition to subjects, the vaccine composition is preferably provided in a lyophilic form, for example, a capsule form. The capsule is provided as an enteric coating containing Eudragate S, Eudragate L, cellulose acetate, cellulose phthalate or hydroxyprolylmethyl cellulose. The capsule may be used as it is or may be administered after it has been reconstituted into a lyophilic material such as a suspension. The reconstitution is preferably performed in a buffer having a pH value suitable for the survival of the transformed recombinant microorganisms. In order to protect the transformed recombinant microorganism and vaccine from gastric acid, it is preferable to administer a sodium bicarbonate formulation every time before administering the vaccine. The vaccine can be selectively prepared for parenteral administration, intranasal administration or intramammary administration.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as illustrative ones and do not limit the scope of the present invention.

Example 1

Preparation of Surface Expression Vector (pKV-Pald-PgsAL-Amylase) Containing repE Mutant Gene In this Example, in order to stabilize an expression vector in host cells, a surface expression vector containing a repE mutant gene and showing an increased expression level of a target protein was constructed.

First, to further increase the expression of a target protein in lactic acid bacteria, a fragment of an aldolase promoter which is a promoter derived from *Lactobacillus casei* was obtained. The aldolase promoter was obtained by PCR using pDT-PgsA-Amylase (disclosed in Korean Patent Publication No. 10-2008-0086161) as a template and primers of SEQ ID NO: 2 and SEQ ID NO: 3.

```
                                        SEQ ID NO: 2:
    5'-cgc gca tgc aat acc cac tta ttg cg-3'

SEQ ID NO: 3:
    5'-cag ttc ttt ttt cat gta gat atc ctc c-3'
```

As a result, a 421-bp DNA fragment containing an aldolase promoter, a SphI restriction enzyme site at the 5' end and a 17-bp N-terminal region of pgsA at the 3'-end was obtained.

Also, a pgsA gene fragment which can be linked with the above-constructed aldolase promoter fragment was obtained by PCR using the above-described vector as a template and primers of SEQ ID NO: 4 and SEQ ID NO: 5.

SEQ ID NO: 4:
5'-gga gga tat cta cat gaa aaa aga act g-3'

SEQ ID NO: 5:
5'-ggc gct ggc ggt cgt ttg g-3'

The obtained DNA fragment was a 782 bp fragment containing a 13 by 3'-end of the aldolase promoter and having pgsA connected directly thereto. The pgsA region of this fragment included a PstI restriction enzyme site.

The two obtained fragments were ligated with each other and subjected to PCR using the primers at both ends, thus obtaining a 1175 by DNA fragment. The DNA fragment was digested with SphI and PstI, thus obtaining a fragment containing the aldolase promoter and the N-terminal portion of pgsA.

pBT:pgsA-Amylase (pAT-PslpA-pgsA-amylase; see Indirect Example of Korean Patent Registration No. 0872042) were digested with SphI and PstI to remove the SlpA7 promoter region and the N-terminal region of pgsA, thus obtaining the backbone of the expression vector.

The aldolase promoter-containing DNA fragment digested with SphI and PstI was ligated with the pBT:PslpA-Amylase digested with the same restriction enzymes, thus constructing pAT-Pald-PgsA-Amylase. The pAT-Pald-PgsA-Amylase vector was subjected to site-directed mutagenesis to substitute the TTA codon encoding the $475^{th}$ amino acid leucine of the repE gene with a TGA stop codon so as to cut 21 C-terminal amino acids of the RepE protein, thus constructing pKV-Pald-PgsA-Amylase having an amino acid sequence of SEQ ID NO: 1 (FIG. 1).

Example 2

Preparation of HPV16 E7 Surface Expression Vector (pKV-Pald-PgsA-E7)

Using the surface expression vector (pKV-Pald-PgsA-Amylase) prepared in Example 1, a gene encoding the HPV16 E7 protein was inserted into the C-terminal end of PgsA, thus preparing a pKV-Pald-PgsA-E7 vector capable of expressing a target protein on the surface of lactic acid bacteria.

For this purpose, the amylase gene fused with pgsA in the pKV-Pald-PgsA-Amylase vector prepared in Example 1 was removed and the HPV16 E7-encoding gene was inserted into the vector. As shown in FIG. 1, a fragment containing the HPV16 E7 gene was obtained by performing PCR using pHAT:PgsA-E7 (Poo et al., Int. J. Cancer, 119: 1702, 2006) as a template and primers of SEQ ID NO: 6 and SEQ ID NO: 7.

SEQ ID NO: 6:
5'-gcg gga tcc cat gga gat aca cct aca ttg c-3'

SEQ ID NO: 7:
5'- acg cag aag cgg tct gat aa -3'

As a result, a 386-bp fragment containing the HPV16 E7 gene was obtained. The fragment contained a BamHI restriction enzyme site at the 5'-end and an XbaI restriction enzyme site at the 3'-end. The obtained DNA fragment was digested with BamHI and XbaI, thus obtaining a 306-bp fragment.

The pKV-Pald-PgsA-Amylase vector was digested with BamHI and XbaI to remove the amylase gene region, thus obtaining a vector fragment.

Figure 2:
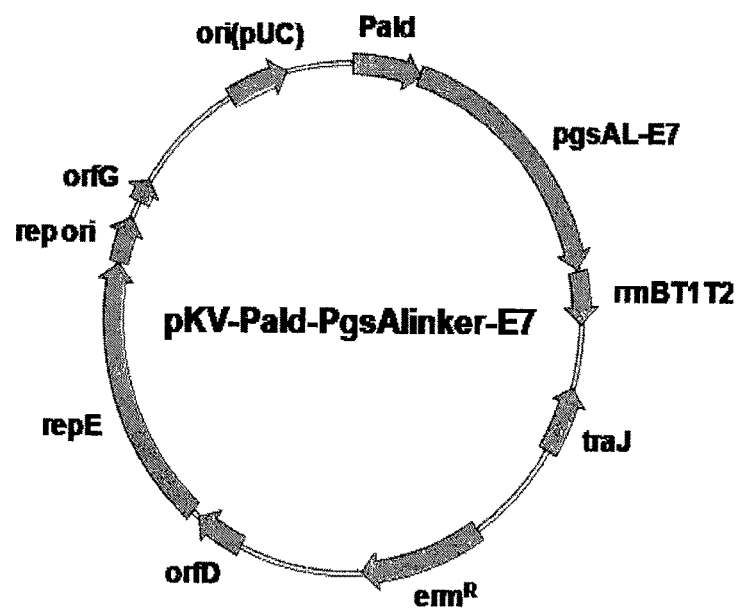
FIG. 2 shows cleavage maps of two kinds of expression vectors expressing the E7 gene on the surface of microorganisms.
Figure 2:
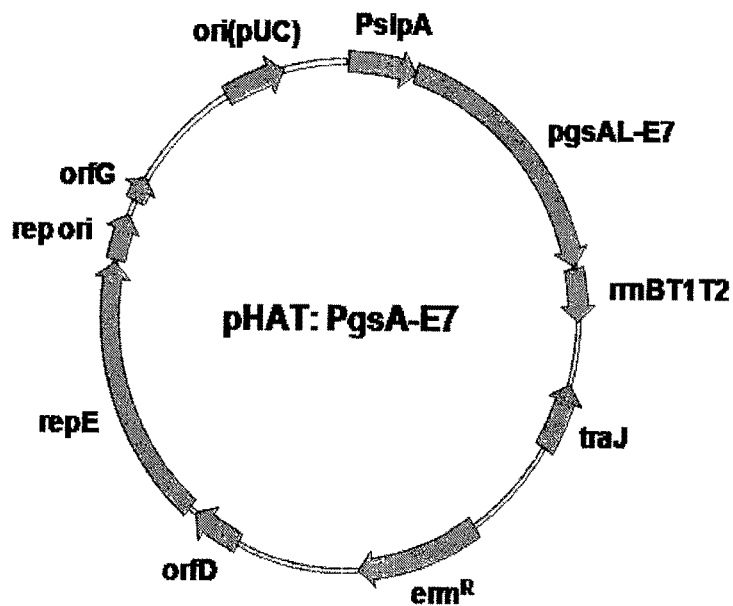

The E7 gene-containing DNA fragment digested with BamHI and XbaI was ligated with the vector digested with the same restriction enzymes, thus constructing pKV-Paid-PgsA-E7 (FIG. 2A).

Example 3

Examination of Expression of pHAT:PgsA-E7 and pKV-Pald-PgsA-E7 in Transformed Lactic Acid Bacteria In this Example, *Lactobacillus casei* was transformed with each of pHAT:PgsA-E7 and pKV-Pald-PgsA-E7, constructed in Example 2. The transformed recombinant *Lactobacillus casei* strain was cultured, and the expression of the E7 protein in the recombinant strain was examined. The expression of the E7 protein fused with PgsA in the transformed recombinant *Lactobacillus casei* strain was examined.

The recombinant *Lactobacillus casei* strain, transformed with each of pHAT:PgsAE7 and pKV-Pald-PgsA-E7, was stationary-cultured in MRS medium (*Lactobacillus* MRS, Becton Dickinson and Company Sparks, USA) at 30° C. to induce the surface expression of the HPV16 E7 protein fused with the C terminal end of the poly-gamma-glutamate synthetase pgsA gene.

The whole cell of the cultured *Lactobacillus casei* strain was subjected to SDS polyacylamide gel electrophoresis and Western blotting using a PgsA-specific antibody.

Specifically, the whole cell of the transformed recombinant *Lactobacillus casei* strain in which the expression of the E7 gene had been induced was denatured with a protein obtained at the same cell concentration so as to prepare a sample. The sample was analyzed by SDS-polyacrylamide gel electrophoresis, and then the protein fractions were transferred to polyvinylidene-difluoride (PVDF) membranes (Bio-Rad). The PVDF membranes to which the protein fractions had been transferred were blocked by shaking in a blocking buffer (50 mM Tris HCl, 5% skim milk, pH 8.0) for 1 hour, and then incubated for 1 hour with rabbit-derived polyclonal anti-PgsA primary antibodies which had been 1000-fold diluted in a blocking buffer. After completion of the incubation, the membranes were washed with buffer solution and incubated for 1 hour with HRP-conjugated anti-rabbit secondary antibodies which had been 10000-fold diluted in a blocking buffer. After completion of the incubation, the membranes were washed with buffer solution, and the washed membranes were color-developed for about 1 minute by the addition of a substrate (lumigen PS-3 acridan, $H_2O_2$), and the specific binding between the PgsA-specific antibody and the fusion protein was observed with a CCD camera (FIG. 3).

Figure 3:
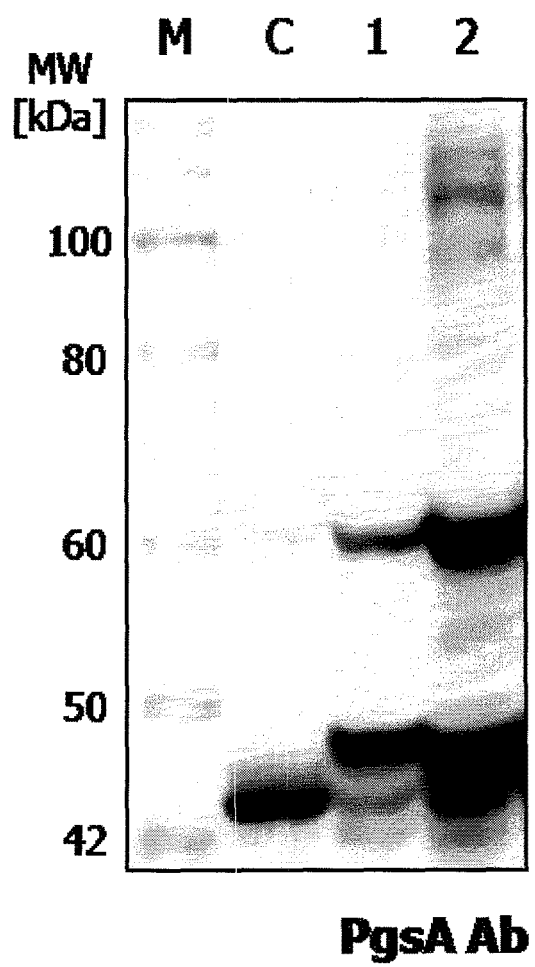
FIG. 3 shows the results of Western blot analysis for the expression of E7 on the surface of lactic acid bacteria transformed with pKV-Pald-PgsA-E7.

In FIG. 3, lane C represents the transformed recombinant *Lactobacillus casei* strain in which only PgsA was expressed (pKV-Pald-PgsA), lane 1 represents the protein expression of the recombinant *Lactobacillus casei* strain transformed with pHAT:PgsA-E7, and lane 2 represents the protein expression of the recombinant *Lactobacillus casei* strain transformed with pKV-Pald-PgsA-E7. As shown in FIG. 3, the expression of a 54.4-kDa PgsA-E7 fusion protein could be observed in lanes 1 and 2 using the PgsA-specific Ab, and it was observed that the expression of the PgsA-E7 fusion protein by pKV-Pald-PgsA-E7 was stronger than the expression of the PgsA-E7 fusion protein by pHAT:PgsA-E7.

In the case of the structure in which the PslpA-PgsA-E7 region of pHAT:PgsA-E7 containing normal RepE was substituted with PaId-PgsA-E7, transformed lactic acid bacteria could not be obtained through the transformed lactic acid bacteria-preparing method conducted in the same manner as described above.

Example 4

Comparison of the Ability to Induce Humoral Immune Responses Between *Lactobacillus* Strains Expressing HPV16 E7 Antigen on the Surface Thereof

*Lactobacillus casei* strains were transformed with each of the surface expression vectors, and the expression of HPV E7 antigen on the surface of the strains was induced in the same manner as in Example 2. Then, the two kinds of transformed recombinant *Lactobacillus casei* strains were compared with respect to the ability of the PgsA-HPVI6 E7 fusion protein to induce humoral immune responses. Also, the two transformed strains having different expression levels of the fusion protein were administered to mice in varying amounts (1, 1/5, and 1/10) and compared with respect to the ability to induce immune responses.

The *Lactobacillus casei* strain was transformed with each of the vectors, cultured, harvested and freeze-dried to prepare powder. The powder was dissolved in buffer (PBS, pH 7.4), and then administered orally to 6-week-old female Balb/c mice.

Figure 4:
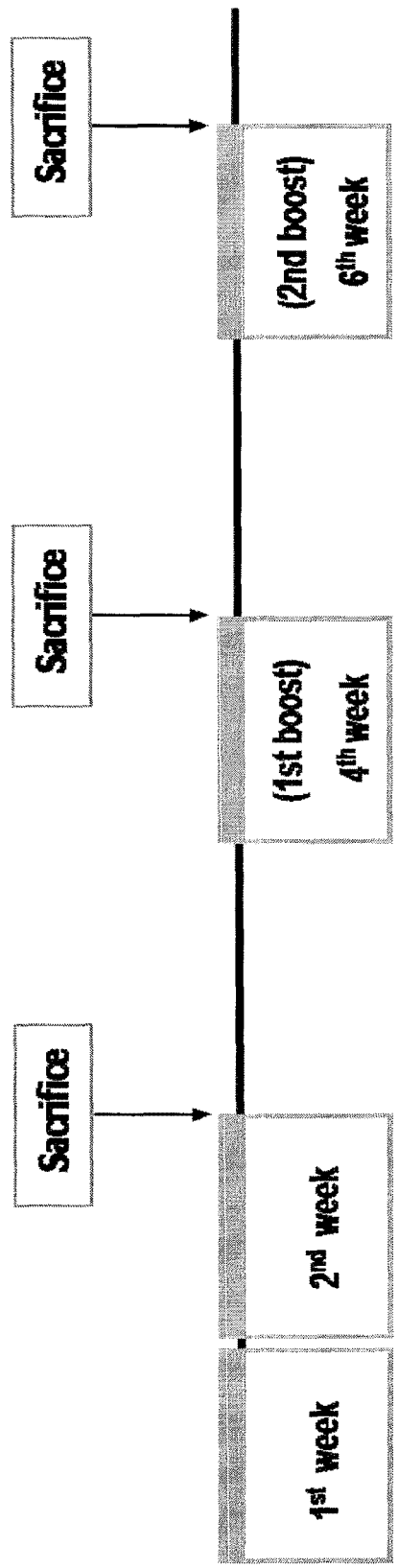
FIG. 4 shows a schedule for administering lactic acid bacteria to mice in order to examine the immune response-inducing ability of transformed recombinant lactic acid bacteria expressing E7 on the surface thereof.

Specifically, each of the freeze-dried powders of the transformed recombinant *Lactobacillus casei* strains (pHAT-E7 and pKV-E7) expressing the HPV16 E7 antigen and of the *Lactobacillus casei* strain (pAT) not expressing the HPV 16 E7 antigen was dissolved in PBS at various concentrations ($5 \times 10^9$ cells/200 µl, $1 \times 10^9$ cells/200 µl, and $5 \times 10^8$ cells/200 µl) and immunized into mice five times a week for 2 weeks (days 0-4, and days 7-11). After 1 week, a first boost was given orally (days 21-25), and after 1 week, a second boost was given orally (days 35-39). In order to measure HPV16 E7-specific IgG antibody in the mouse serum and HPV16 E7-specific IgA antibody secreted from the mouse mucosa, an intestinal wash and a vaginal wash were collected from each of the mice at 14 days, 28 days and 42 days (FIG. 4). Specifically, blood was obtained from the mouse eye using a heparin-coated microcapillary tube, and an intestinal wash and a vaginal wash were collected in amounts of 0.8 ml and 250 µl, respectively, using 1 mM PMSF-containing PBS buffer. Then, each of the washes was centrifuged at 13,000 rpm for 20 minutes, and the supernatant was isolated and subjected to ELISA analysis.

In the ELISA analysis, the HPV16 E7 protein was diluted in coating buffer (0.1 M sodium carbonate, 0.02% sodium azide, pH 9.6) at a concentration of 500 ng/100 µl per well, and then 100 µl of the dilution was added to 96-well ELISA plates and incubated at 4° C. overnight. The ELISA plates were washed three times by adding PEST (PBS+0.05% Tween20) thereto in an amount of 300 µl/well, and then the ELISA plates were blocked with 100 µl of 5% skim milk at 37° C. for 1 hour, followed by removal of the blocking buffer. Then, the plates were washed three times with PBST, and 100 µl of each of the diluted serum and mucosa washes was added to the plates. After the samples were added, they were incubated at 37° C. for 2 hours, and then washed three times with washing buffer. Then, horseradish peroxidase-conjugated anti-mouse IgG or IgA antibody was diluted at 1:5000, added to each well and incubated at 37° C. for 1 hour. Then, each well was washed with washing buffer and color-developed with TMB solution, and the color development was stopped with 2.5 M sulfuric acid. The amount of HPV16 E7-specific antigen was analyzed by measurement with an ELISA reader at 450 nm.

Figure 5:
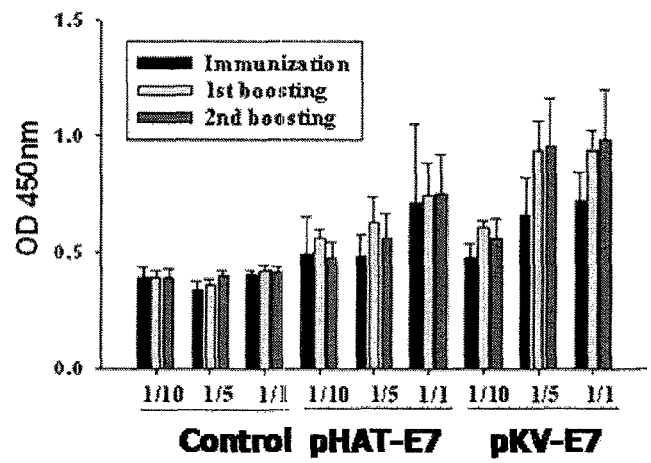
FIG. 5 shows changes in IgG and IgA upon oral administration of transformed recombinant lactic acid bacteria expressing E7 on the surface thereof.
Figure 5:
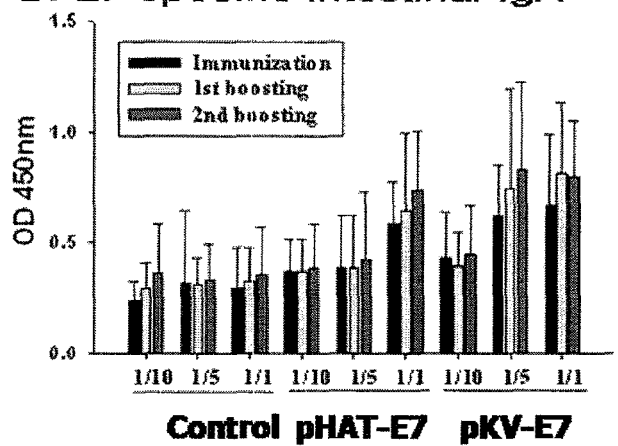
Figure 5:
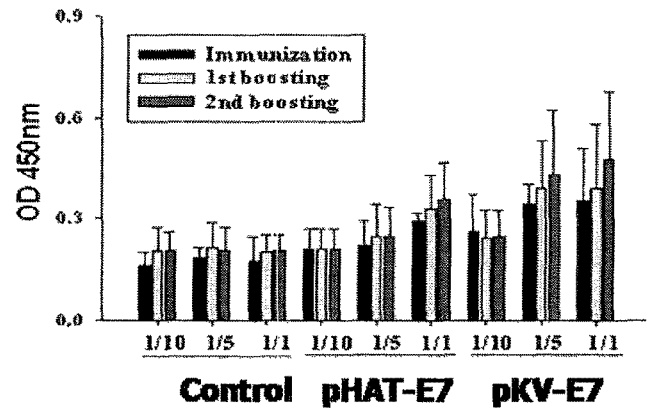

As a result, as shown in FIG. 5A, when the average OD value of E7-specific serum IgG was measured after 2 weeks of immunization, the groups administered with each of pAT-E7 and pKV-E7 showed OD values higher than that of the pAT control group. Also, it was observed that the amount of the E7-specific antibody increased depending on the amount of strain administered. The average OD value of E7-specific serum IgG after the first boosting was increased in both the pAT-E7administered group and the pKV-E7-administered group compared to the value measured after 2 weeks of immunization and indicated a boosting effect. The average OD value of E7-specific serum IgG after the second boosting also indicated a boosting effect in the two administered groups. Particularly, in the case of the pKV-E7-administered group, the surface expression of E7 fusion protein of which was significantly higher than that of the pAT-E7-administered group, the group administered with pKV-E7 in an amount of 1/5 showed an IgG boosting effect similar to that of the group administered with pAT-E7 in an amount of 1/1.

Meanwhile, in order to measure mucosal immune responses, the E7-specific IgA antibodies in the intestinal and vaginal washes were measured by ELISA. As a result, as shown in FIG. 5B and FIG. 5C, the average OD value (i.e., E7-specific IgA) after 2 weeks of immunization was increased in both the pAT-E7-administered group and the pKV-E7-administered croup compared to the pAT control group, and the E7-specific antibody was increased depending on the amount of strain administered. The average OD value after the first boosting was further increased, and the second boosting effect was slightly higher than the first boosting effect.

In conclusion, when the inventive transformed recombinant *Lactobacillus casei* strains expressing HPV16 E7 were administered orally to the mice, they could induce HPV16 E7-specific humoral immune responses (serum IgG induction) and mucosal immune responses (intestinal/vaginal IgA induction). Particularly, the pKV-E7-administered group expressing a higher level of E7 could more effectively induce immune responses compared to the pAT-E7-administered group.

Example 5

Comparison of the Ability to Induce Cellular Immune Responses Between *Lactobacillus* Strains Expressing HPV16 E7 Antigen on the Surface Thereof In order to examine whether two kinds of transformed recombinant *Lactobacillus casei* strains (pHAT-E7 and pKV⁻E7) having different surface expression levels of HPV 16 E7 antigen differ with respect to the ability to induce E7 antigen-specific CD8+ T cell-mediated immune responses and T cell immune responses, each of intracellular cytokine staining and IFN-γ ELISPOT was carried out using mice administered orally with each of the strains, thus examining the ability of the strains to induce cellular immune responses.

For this purpose, splenocytes were isolated from mice administered orally with each of the transformed recombinant *Lactobacillus casei* strains expressing E7 on the surface thereof as mentioned as in Example 4. The splenocytes were suspended in 10% FBS-containing RPMI-1640 medium and seeded into 24-well plates at a density of $5 \times 10^6$ cells/well. Each well was treated with an MHC class I epitope-containing E7 peptide (a.a 49-57, AniGen, Korea) and GolgiPlug (BD Biosciences), and the cells were cultured 37° C. for 16 hours. The cultured cells were stained with phycoerythrin (PE)-conjugated monoclonal rat anti-mouse CD8 antibody at 4° C. for 40 minutes, and IFN-γ in the cells was stained with FITC-conjugated monoclonal rat anti-mouse IFN-γ antibody using the Cytofix/Cytoperm kit.

Figure 6:
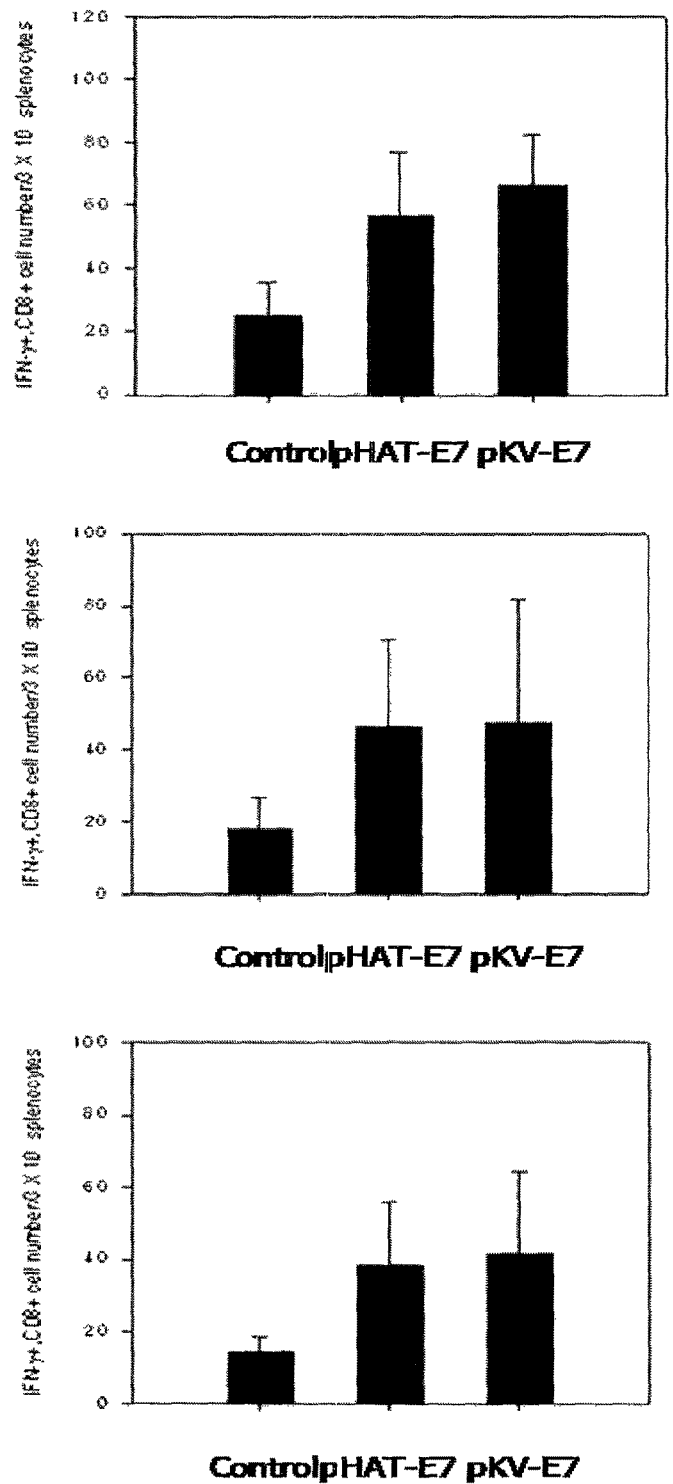
FIG. 6 shows the results of analysis of E7-specific IFN-gamma secretion upon oral administration of transformed recombinant lactic acid bacteria expressing E7 on the surface thereof.

As described above, after the mice had been administered orally with each of the two recombinant *Lactobacillus casei* strains, intracellular cytokine staining was carried out to measure the number of E7-specific IFN-γ-secreting CD8+ T cells. As a result, as can be seen in FIG. 6, the number of E7-specific IFN-γ-secreting CD8+ T 25 cell precursors was increased by the transformed recombinant *Lactobacillus casei* strains expressing E7. Particularly, in the initial stage at which immune responses were induced, it was seen that the cell-mediated immune responses induced by the recombinant *Lactobacillus casei* pKV-E7 strain having a higher surface expression level were slightly increased compared to those induced by the pHAT-E7 lactic acid bacteria, but the cell-mediated immune responses induced by the pHAT-E7 lactic acid bacteria were increased to a level similar to that of the pKV-E7 strain after boosting.

In order to examine the induction of E7-specific T cell immune responses, IFN-γ ELISPOT was carried out to measure the total number of T cells secreting IFN-γ specifically to E7 peptide stimulation. For this purpose, one day before isolation of splenocytes, a 24-well plate was coated with anti-mouse IFN-γ capture antibody, and the splenocytes isolated at the day of the experiment were seeded into each well of the plate at a density of $2 \times 10^5$ cells/well. Each well seeded with the cells was treated with the E7 peptide or PHA-M, and the cells were cultured for 2 days. After 2 days, the content of the plate was removed and washed twice with distilled water and three times with 0.05% tween-20-containing PBS, and biotinylated anti-mouse IFN-γ was added to each well of the plate and incubated for 2 hours at room temperature. After completion of the incubation, the content of the plate was removed, each well was washed three times with 0.05% tween-20-containing PBS, and then streptavidin-HRP was added to each well of the plate and incubated at room temperature for 1 hour. After the content of the plate has been removed, each well was washed four times with 0.05% tween-20-containing PBS and twice with PBS. Then, a substrate was added to each well, and color development in each well was observed for 5-60 minutes. The color development reaction was stopped by distilled water, and the number of spots in each well was measured using the ELISPOT reader.

As a result, as shown in FIG. 6, in the mice administered orally with the recombinant lactic acid bacteria transformed with pHAT-E7 or pKV-E7, the number of cells secreting IFN-γ specifically to the E7 peptide was increased. Also, the number of IFN-γ-secreting cells in the group administered with the recombinant *Lactobacillus casei* strain transformed with pKV-E7 was slightly larger than that in the group administered with the recombinant *Lactobacillus casei* strain transformed with pHAT-E7.

Example 6

Tumor Cell Challenge in Mice Immunized with *Lactobacillus* Expressing HPV E7 Antigen on the Surface Thereof In order to confirm the anticancer effect of two kinds of transformed recombinant *Lactobacillus* strains (pHAT-E7 and pKV-E7) having different surface expression levels of HPV 16 E7 antigen and to confirm the anticancer effect according to the amount thereof, tumor cell challenge was carried out using a TC-1 tumor cell model expressing the E7 protein.

For this purpose, 6-8-week-old female C57BL/6 mice were divided into several groups, each consisting of 5 animals, and each of the transformed recombinant *Lactobacillus casei* strains expressing E7 on the surface thereof was administered orally to the mice. The oral administration was performed five times a week, and the mice were treated according to the following schedule: 1 week of oral administration followed by 1 week of rest, then 1 week of first boosting followed by 1 week of rest, and then 1 week of second boosting. After 1 week of oral administration, $2 \times 10^4$ TC-1 tumor cells were injected subcutaneously into the left thigh of each mouse to induce tumors. The size of the formed tumor was measured three times a week using calipers.

Figure 7:
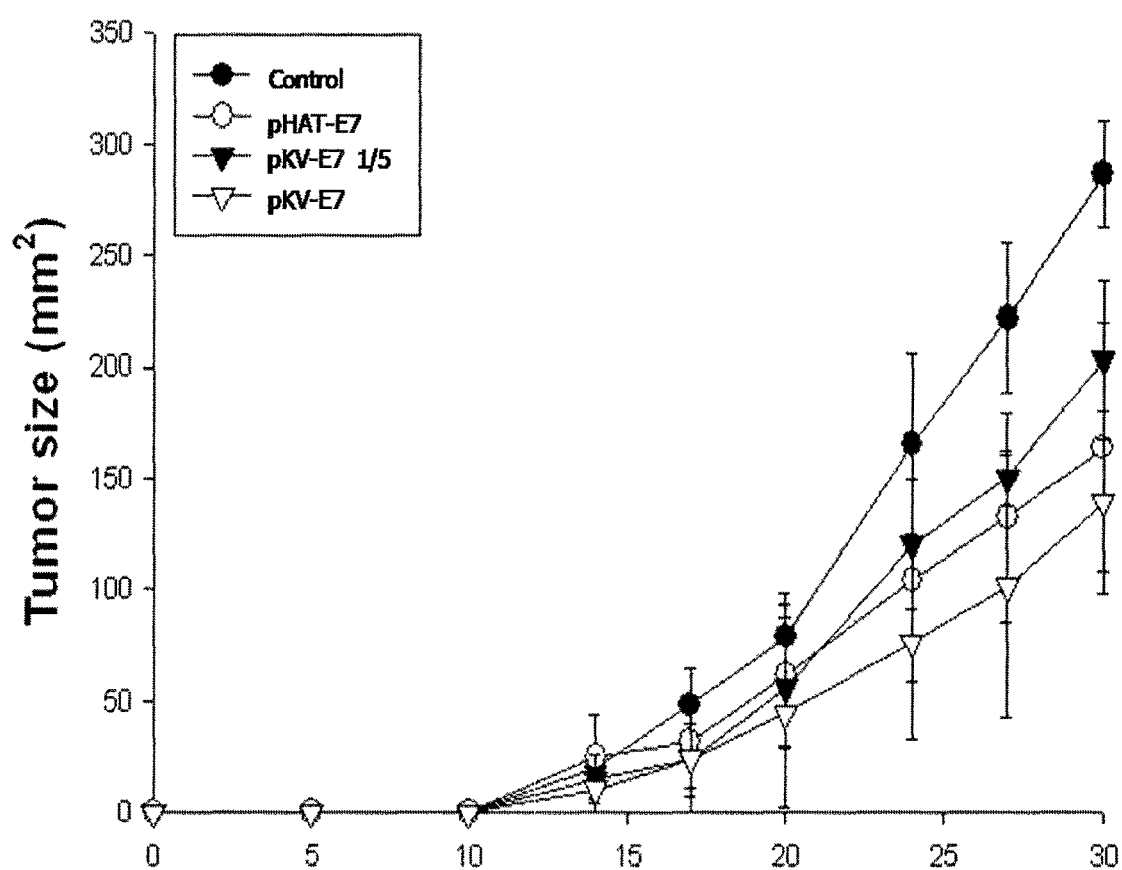
FIG. 7 shows the results of a tumor challenge assay conducted by orally administrating transformed recombinant lactic acid bacteria expressing E7 on the surface thereof and determining whether the tumor size increased.

As a result, as can be seen in FIG. 7, in the group administered orally with the recombinant *Lactobacillus casei* strain transformed with pHAT-E7 or pKV-E7, the size of the formed tumor was about 50 percent smaller than the tumor size of the control group. Also, the group administered with the recombinant *Lactobacillus casei* strain pKV-E7 in a reduced amount of 1/5 showed a tumor size smaller than that of the control group.

Example 7

Preparation of Immunized Lactic Acid Bacteria (pKV-Pald-PgsA-E7(Rb)) Expressing on the Surface Thereof a Protein Having Amino Acid Mutations Introduced into HPV Type 16 E7

If cells are infected with papillomavirus, the expressed E7 protein can bind to the retinoblastoma growth suppressor protein (pRb) to cause cancer. For this reason, mutations in the base sequence of a region binding to the pRb of the E7 gene were induced. The mutation-induced E7(Rb) gene was fused to the end of PgsA using a pKV shuttle vector which is stably expressed in *E. coli* and lactic acid bacteria, thereby preparing a pKV-Pald-PgsA-E7(Rb) vector capable of being expressed on the surface of lactic acid bacteria.

Examination results for the Rb-binding site of HPV type 16 E7 revealed that the retinoblastoma growth suppressor protein (pRb)-binding site (DLxCxE) consists of amino acid residues 21-26 of the HPV16 E7 gene (Smahel M. et al., *Virology*, 281: 231, 2001). In order to substitute all the $21^{st}$ (D), $24^{th}$ (C) and $26^{th}$ (E) amino acids among the amino acid residues 21-26 with glycine, the ability of the E7 protein to bind to the pRb protein was removed by point mutagenesis using primers. Specifically, PCR was performed using the pKV-Pald-PgsA-E7 vector prepared in Example 2 as a template and each of a primer set of SEQ ID NOS: 8 and 9 and a primer set of SEQ ID NOS: 10 and 11.

```
                                       SEQ ID NO: 8:
5'-tct gga tcc atg cat gga gat aca cct ac-3'

SEQ ID NO: 9:
5'-ttg ccc ata acc gta gag acc agt tgt c-3'

SEQ ID NO: 10:
5'-act ggt ctc tac ggt tat ggg caa tta aat g-3'

SEQ ID NO: 11:
5'-cat tct aga tca tta tgg ttt ctg aga aca g-3'
```

Figure 8:
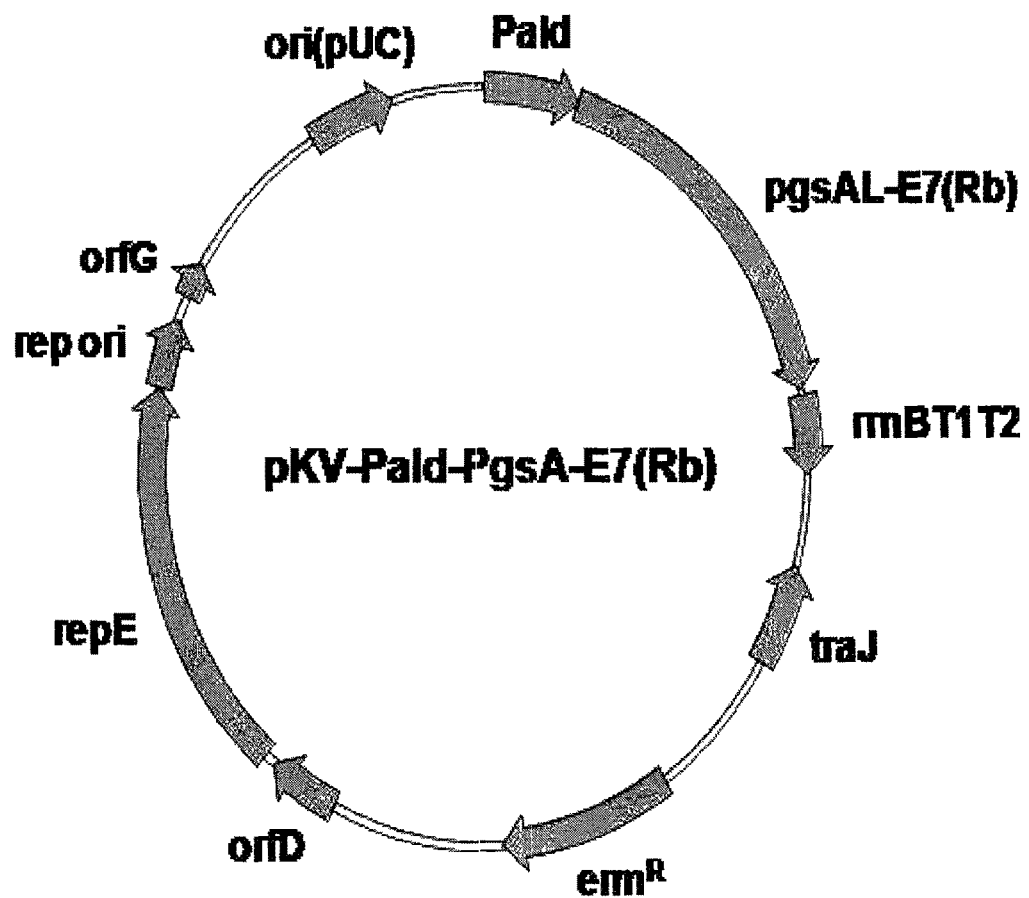
FIG. 8 shows a cleavage map of an expression vector expressing an E7(Rb) gene on the surface of microorganisms.

As a result, a 87-bp DNA fragment containing the HPV16 E7 gene was obtained by the primers of SEQ ID NOS: 8 and 9 and contained a BamHI restriction enzyme site at the 5' end. Also, a 249-bp DNA fragment was obtained by the primers of SEQ ID NOS: 10 and 11 and contained an XbaI restriction enzyme site at the 3'end. The two obtained DNA fragments were mixed with each other and subjected to 10 PCR cycles consisting of 30 sec at 95° C., 30 sec at 42° C. and 30 sec at 72° C. Then, primers of SEQ ID NOS: 8 and 11 were added to the PCR product, which was then subjected to PCR (30 sec at 95° C., 30 sec at 53° C. and 30 sec at 72° C.). The obtained 312-bp DNA fragment contained a BamHI restriction enzyme site at the 5' end and an XbaI restriction enzyme site at the 3' end. The fragment was digested with the restriction enzymes BamHI and XbaI to obtain a 306-bp E7(Rb) mutant gene fragment. pKV-Paid-PgsA-Amylase was digested with BamHI and XbaI to remove the amylase gene region, thus obtaining a vector region. The E7(Rb) mutant gene-containing DNA fragment digested with BamHI and XbaI was ligated with the vector digested with the same restriction enzymes, thus constructing pKV-Pald-PgsA-E7(Rb) (FIG. 8).

The pKV-Pald-PgsA-E7(Rb) construct was transformed into *Lactobacillus casei* by electroporation, thus obtaining lactic acid bacteria transformed with the construct.

Example 8

Examination of Expression of pKV-Pald-PgsA-E7(Rb) in Transformed Lactic Acid Bacteria In order to examine whether the PgsA-E7 fusion protein having mutations at the Rb binding site is expressed in the recombinant *Lactobacillus casei* transformed with the obtained pKV-Pald-PgsA-E7(Rb) vector for expression on the surface of lactic acid bacteria, the following experiment was carried out.

Figure 9:
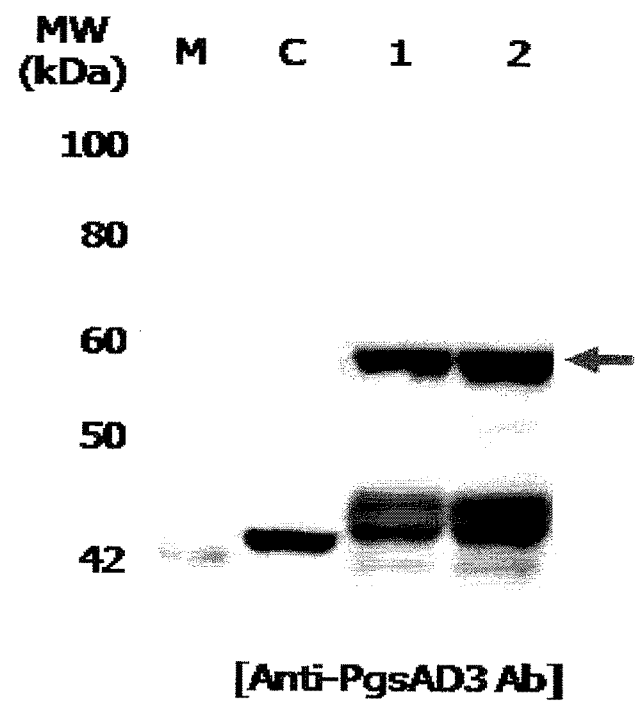
FIG. 9 shows the results of analysis of the expression of E7(Rb) on the surface of recombinant lactic acid bacteria transformed with pKV-Pald-PgsA-E7(Rb).
Figure 9:
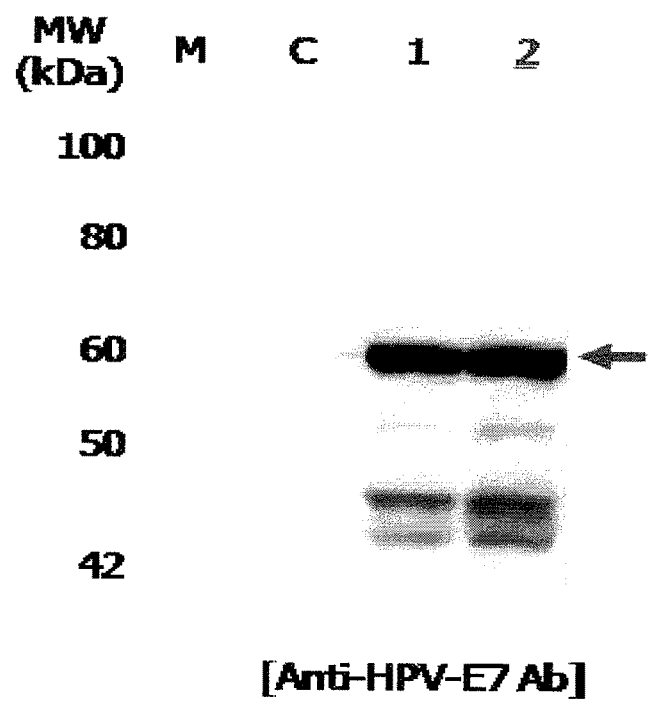

The transformed recombinant *Lactobacillus casei* was stationary-cultured in MRS medium (*Lactobacillus* MRS, Becton Dickinson and Company Sparks, USA) at 30° C., and the microbial cells were collected and analyzed by Western blotting in the same manner as in Example 3. As a result, it was confirmed that the fusion protein was expressed in the microbial strain. Specifically, Western blotting was performed using PgsA-specific antibody and HPV16 E7-specific antibody (E7 monoclonal Ab, Invitrogen, USA) and, as a result, as shown in FIG. 9, the expression of an about 54.7-kDa mutant E7 protein fused with PgsA was confirmed.

Example 9

Induction of Humoral Immune Responses by *Lactobacillus* Expressing HPV16 E7(Rb) Mutant Antigen on the Surface Thereof The recombinant *Lactobacillus casei* strain confirmed to express the PgsA-fused E7 mutant protein thereon was administrated orally to mice in order to examine whether humoral immune responses were induced. For this purpose, *Lactobacillus casei* was transformed with the vector, cultured, and then freeze-dried to prepare powder. The powder was dissolved in buffer (PBS, pH 7.4) and administered orally to 6-week-old female Balb/c mice.

Specifically, each of the powders of the transformed recombinant *Lactobacillus casei* strain (E7-Rb) expressing HPVI6 E7(Rb) and of a *Lactobacillus casei* strain (L525) not expressing HPV16 E7(Rb) was dissolved in PBS at a concentration of $2$-$5 \times 10^9$ cells/200 µl, and then immunized into mice five times a week for 2 weeks (days 0-4, and days 7-11). After one week, a first boost was given orally (days 21-25), and after one week, a second boost was given orally (days 35-39 days). In order to measure HPV16 E7-specific IgG antibody in the mouse serum and HPV 16 E7-specific IgG antibody secreted from the mouse mucosa, an intestinal wash and a vaginal wash were collected from each mouse at days 14, 28 and 42 as shown in FIG. 3. As described in Example 4, blood was obtained from the mouse eye using a heparin-coated microcapillary tube, and an intestinal wash and a vaginal wash were collected from each mouse in amounts of 0.8 ml and 250 µl, respectively, using 1 mM PMSF-containing PBS washing buffer. Each of the collected washes was centrifuged at 13,000 rpm for 20 minutes, and the supernatant was isolated and analyzed by ELISA in the same manner as in Example 4.

Figure 10:
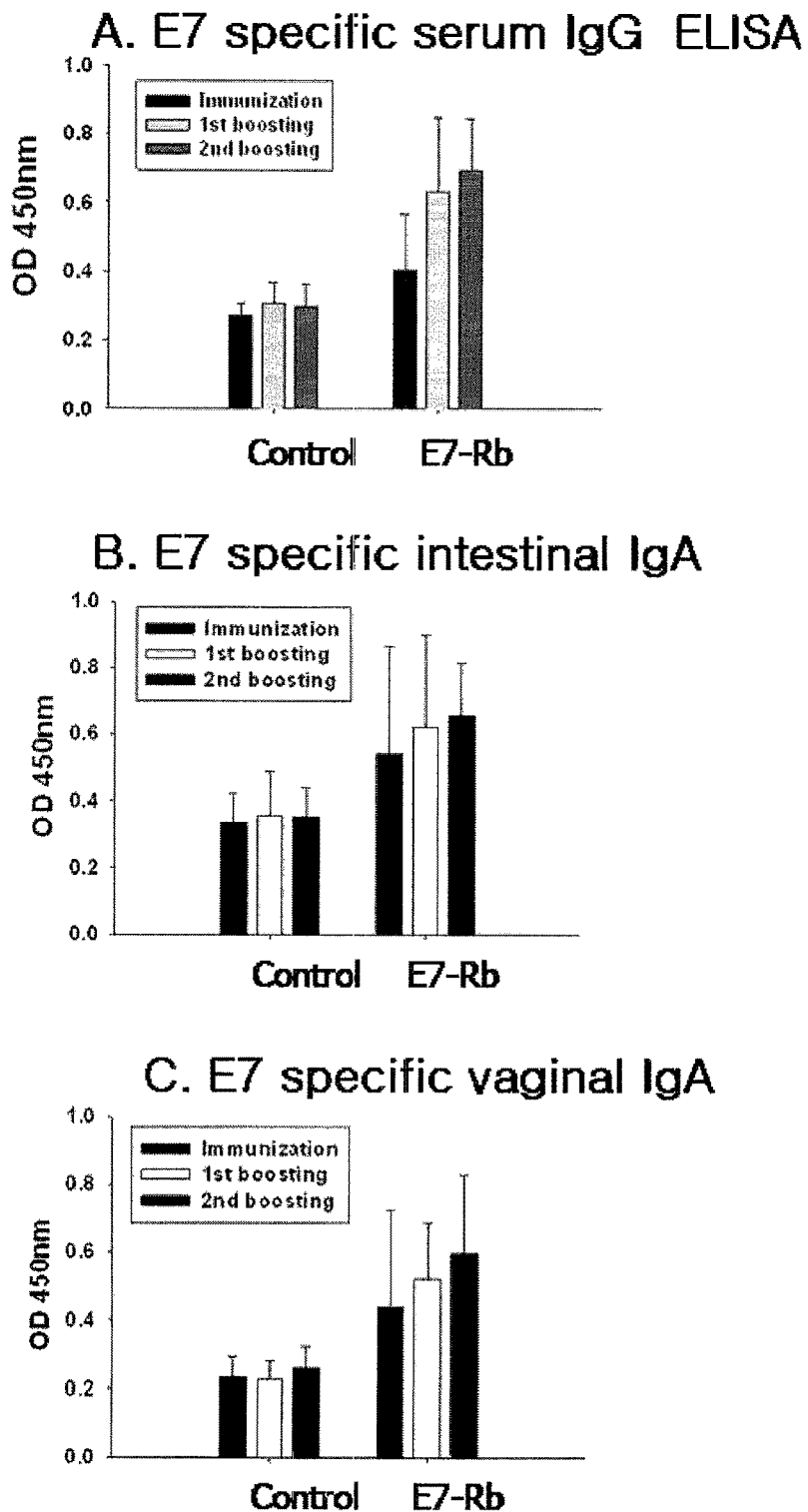
FIG. 10 shows the results of E7-specific ELISA.

As a result, as shown in FIG. 10A, when the average OD value of E7-specific serum IgG after 2 weeks of immunization was measured, the group administered with E7-Rb showed an OD value higher than that of the group administered with L525 (negative control group). The average OD value of E7-specific serum IgG after the first boosting was increased in the E7-Rb-administered group compared to the OD value measured after 2 weeks of immunization and indicated a boosting effect. The average OD value of E7-specific serum IgG also indicated a boosting effect. However, the L525-administered group did not show a special boosting effect. Also, in order to measure humoral immune responses induced in the mucosa, E7-specific IgA antibody in each of the intestinal and vaginal was measured by ELISA. As a result, as shown in FIG. 10B and FIG. 10C, the average OD value (E7-specific IgA) after 2 weeks of the immunization was increased in the E7-Rb-administered group compared to the L525-administered group (negative control group). Also, the average OD value after the first boosting was increased compared to the value measured after 2 weeks of the immunization, and the second boosting effect was increased compared to the first boosting effect.

In conclusion, when the recombinant *Lactobacillus casei* strain transformed with E7-Rb was administered orally to the mice, it could induce all HPV16 E7-specific systemic humoral immune responses (serum IgG induction) and mucosal humoral immune response (intestinal/vaginal IgA induction).

Example 10

Induction of Cellular Immune Responses by *Lactobacillus* Expressing HPV16 E7(Rb) Mutant Antigen on the Surface Thereof In order to whether the transformed recombinant *Lactobacillus* strain (E7-Rb) expressing the HPV 16 E7(Rb) mutant antigen on the surface thereof has the ability to induce E7(Rb) antigen-specific T cell-mediated immune responses, IFN-γ ELISPOT was carried out using mice administered orally with the strain, thus examining the ability of the strain to induce cellular immune responses. For this purpose, the transformed recombinant *Lactobacillus casei* strain expressing E7(Rb) on the surface thereof, constructed in Example 7, was administered orally to mice, and splenocytes were isolated from the mice. The isolated splenocytes were suspended in 10% FBS-containing RPMI-1640 medium and seeded into each well of a 24-well plate at a density of $5 \times 10^6$ cells. Each well was treated with an MHC class I epitopecontaining E7 peptide (a.a 49-57, AniGen, Korea) and GolgiPlug (BD Biosciences), and the cells were cultured at 37° C. for 16 hours. The cultured cells were stained with phycoerythrin(PE)-conjugated monoclonal rat anti-mouse CD8 antibody at 4° C. for 40 minutes, and IFN-γ in the cells was stained with FITC-conjugated monoclonal rat anti-mouse IFN-γ antibody using the Cytofix/Cytoperm kit.

Figure 11:
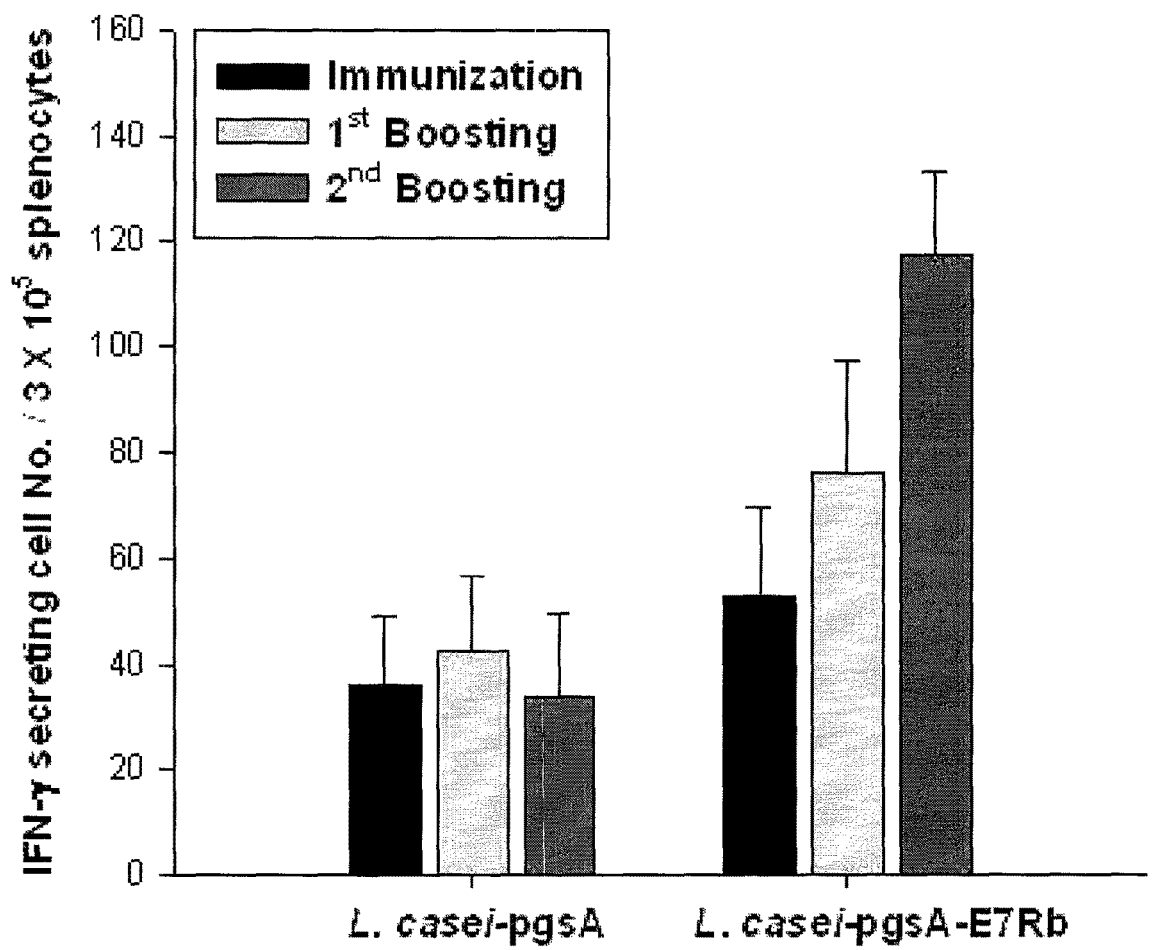
FIG. 11 shows the results of analysis of E7(Rb)-specific IFN-gamma secretion upon oral administration of transformed lactic acid bacteria expressing E7(Rb) on the surface thereof.

As described above, each of the two recombinant *Lactobacillus casei* strains was administered orally to the mice, and then intracellular cytokine staining was carried out to measure the number of E7(Rb)-specific IFN-γ-secreting CD8+ T cells. As a result, as can be seen in FIG. 11, the number of E7(Rb)-specific IFN-γ-secreting 15 CD8+ T cell precursors was increased by the transformed recombinant *Lactobacillus casei* expressing E7(Rb). Particularly, in the initial stage at which immune responses were induced, it was seen that the cell-mediated immune responses induced by the recombinant *Lactobacillus casei* pKV-E7(Rb) strain having a higher surface expression level were slightly increased compared to those induced by the pHAT-E7(Rb) lactic acid bacteria, but the cell-mediated immune responses induced by the pHAT-E7(Rb) lactic acid bacteria were increased to a level similar to that of the pKV-E7(Rb) strain after boosting.

In order to examine the induction of E7-specific T cell immune responses, IFN-γ ELISPOT was carried out to measure the total number of T cells secreting IFN-γ specifically to E7 peptide stimulation.

For this purpose, one day before isolation of splenocytes, a 24-well plate was coated with anti-mouse IFN-γ capture antibody, and the splenocytes isolated at the day of the experiment were seeded into each well of the plate at a density of 2×10$^5$ cells/well. Each well seeded with the cells was treated with the E7 peptide or PHA-M, and the cells were cultured for 2 days. After 2 days, the content of the plate was removed and washed twice with distilled water and three times with 0.05% tween-20-containing PBS, and biotinylated anti-mouse IFN-γ was added to each well of the plate and incubated for 2 hours at room temperature. After completion of the incubation, the content of the plate was removed, each well was washed three times with 0.05% tween-20containing PBS, and then streptavidin-HRP was added to each well of the plate and incubated at room temperature for 1 hour. After the content of the plate had been removed, each well was washed four times with 0.05% tween-20-containing PBS and twice with PBS. Then, a substrate was added to each well, and the observation of color development in each well was performed for 5-60 minutes. The color development reaction was stopped by distilled water, and the number of spots in each well was measured using the ELISPOT reader.

As a result, as shown in FIG. 11, in the mice administered orally with the recombinant lactic acid bacteria transformed with pHAT-E7(Rb) or pKV-E7(Rb), the number of cells secreting IFN-γ specifically to the E7 peptide was increased. Also, the number of IFN-γ-secreting cells in the group administered with the recombinant *Lactobacillus casei* strain transformed with pKV-E7(Rb) was slightly larger than that in the group administered with the recombinant *Lactobacillus casei* strain transformed with pHAT-E7(Rb).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, recombinant lactic acid bacteria, transformed with the inventive surface expression vector and expressing the human papillomavirus (HPV) antigen protein on the surface thereof, and a composition containing the recombinant lactic acid bacteria as an active ingredient, can be used as a vaccine for treatment of cervical cancer. The transformed recombinant strain constitutively expressing a high level of the HPV antigen is very effective, because it can proliferate in a large amount in an economic manner and can be applied as an oral vaccine or directly to the vagina.

What is claimed is:

1. A surface expression vector for preparing human papillomavirus (HPV) immunogenic compositions, the surface expression vector comprising a gene encoding a repE mutant protein consisting of the amino acid sequence of SEQ ID NO:1, a lactic acid bacteria-derived aldolase promoter, a poly-gamma-glutamate synthetase complex gene for the surface expression, and a gene which is linked with the poly-gamma-glutamate synthetase complex gene and encodes a tumor induction-associated antigen protein of human papillomavirus.

2. The surface expression vector according to claim 1, wherein the tumor induction-associated antigen protein of HPV is E7 or E7(Rb) of HPV.

3. The surface expression vector according to claim 1, wherein the poly-gamma-glutamate synthetase complex gene is selected from the group consisting of pgsB, pgsC and pgsA.

4. A recombinant microorganism transformed with the vector according to claim 1.

5. The recombinant microorganism according to claim 4, wherein the microorganism is lactic acid bacteria.

6. A immunogenic composition for administration to a patient with cervical cancer, the immunogenic composition comprising the transformed recombinant microorganism according to claim 4 as an active ingredient.

7. A method for preparing a microorganism having an HPV antigen expressed on the surface thereof, the method comprising the steps of: culturing the recombinant microorganism according to claim 4 to express an HPV antigen on the surface of the microorganism; and collecting the recombinant microorganism having the HPV antigen expressed on the surface thereof.

8. A immunogenic composition for treating cervical cancer, the immunogenic composition comprising the recombinant microorganism having the HPV antigen expressed on the surface thereof prepared by the method of claim 7 as an active ingredient.

9. The vaccine according to claim 6, wherein the immunogenic composition is administered orally.

* * * * *

SEQUENCE LISTING

<160> NUMBER OF SEQ ID NOS: 11

<210> SEQ ID NO 1
<211> LENGTH: 474
<212> TYPE: PRT
<213> ORGANISM: Artificial
<220> FEATURE:
<223> OTHER INFORMATION: RepE variant

<400> SEQUENCE: 1

```
Met Asn Ile Pro Phe Val Val Glu Thr Val Leu His Asp Gly Leu Leu
1               5                   10                  15

Lys Tyr Lys Phe Lys Asn Ser Lys Ile Arg Ser Ile Thr Thr Lys Pro
            20                  25                  30

Gly Lys Ser Lys Gly Ala Ile Phe Ala Tyr Arg Ser Lys Ser Ser Met
        35                  40                  45

Ile Gly Gly Arg Gly Val Val Leu Thr Ser Glu Glu Ala Ile Gln Glu
    50                  55                  60

Asn Gln Asp Thr Phe Thr His Trp Thr Pro Asn Val Tyr Arg Tyr Gly
65                  70                  75                  80

Thr Tyr Ala Asp Glu Asn Arg Ser Tyr Thr Lys Gly His Ser Glu Asn
                85                  90                  95
```

-continued

Asn Leu Arg Gln Ile Asn Thr Phe Phe Ile Asp Phe Asp Ile His Thr
            100                 105                 110
Ala Lys Glu Thr Ile Ser Ala Ser Asp Ile Leu Thr Thr Ala Ile Asp
            115                 120                 125
Leu Gly Phe Met Pro Thr Met Ile Ile Lys Ser Asp Lys Gly Tyr Gln
130                 135                 140
Ala Tyr Phe Val Leu Glu Thr Pro Val Tyr Val Thr Ser Lys Ser Glu
145                 150                 155                 160
Phe Lys Ser Val Lys Ala Ala Lys Ile Ile Ser Gln Asn Ile Arg Glu
                165                 170                 175
Tyr Phe Gly Lys Ser Leu Pro Val Asp Leu Thr Cys Asn His Phe Gly
            180                 185                 190
Ile Ala Arg Ile Pro Arg Thr Asp Asn Val Glu Phe Phe Asp Pro Asn
            195                 200                 205
Tyr Arg Tyr Ser Phe Lys Glu Trp Gln Asp Trp Ser Phe Lys Gln Thr
            210                 215                 220
Asp Asn Lys Gly Phe Thr Arg Ser Ser Leu Thr Val Leu Ser Gly Thr
225                 230                 235                 240
Glu Gly Lys Lys Gln Val Asp Glu Pro Trp Phe Asn Leu Leu His
                245                 250                 255
Glu Thr Lys Phe Ser Gly Glu Lys Gly Leu Ile Gly Arg Asn Asn Val
            260                 265                 270
Met Phe Thr Leu Ser Leu Ala Tyr Phe Ser Ser Gly Tyr Ser Ile Glu
            275                 280                 285
Thr Cys Glu Tyr Asn Met Phe Glu Phe Asn Asn Arg Leu Asp Gln Pro
290                 295                 300
Leu Glu Glu Lys Glu Val Ile Lys Ile Val Arg Ser Ala Tyr Ser Glu
305                 310                 315                 320
Asn Tyr Gln Gly Ala Asn Arg Glu Tyr Ile Thr Ile Leu Cys Lys Ala
                325                 330                 335
Trp Val Ser Ser Asp Leu Thr Ser Lys Asp Leu Phe Val Arg Gln Gly
            340                 345                 350
Trp Phe Lys Phe Lys Lys Arg Ser Glu Arg Gln Arg Val His Leu
            355                 360                 365
Ser Glu Trp Lys Glu Asp Leu Met Ala Tyr Ile Ser Glu Lys Ser Asp
370                 375                 380
Val Tyr Lys Pro Tyr Leu Val Thr Thr Lys Lys Glu Ile Arg Glu Val
385                 390                 395                 400
Leu Gly Ile Pro Glu Arg Thr Leu Asp Lys Leu Leu Lys Val Leu Lys
                405                 410                 415
Ala Asn Gln Glu Ile Phe Phe Lys Ile Lys Pro Gly Arg Asn Gly Gly
            420                 425                 430
Ile Gln Leu Ala Ser Val Lys Ser Leu Leu Leu Ser Ile Ile Lys Val
            435                 440                 445
Lys Lys Glu Glu Lys Glu Ser Tyr Ile Lys Ala Leu Thr Asn Ser Phe
            450                 455                 460
Asp Leu Glu His Thr Phe Ile Gln Glu Thr
465                 470

<210> SEQ ID NO 2
<211> LENGTH: 26
<212> TYPE: DNA
<213> ORGANISM: Artificial
<220> FEATURE:
<223> OTHER INFORMATION: primer

```
<400> SEQUENCE: 2
cgcgcatgca atacccactt attgcg                                        26

<210> SEQ ID NO 3
<211> LENGTH: 28
<212> TYPE: DNA
<213> ORGANISM: Artificial
<220> FEATURE:
<223> OTHER INFORMATION: primer

<400> SEQUENCE: 3
cagttctttt ttcatgtaga tatcctcc                                      28

<210> SEQ ID NO 4
<211> LENGTH: 28
<212> TYPE: DNA
<213> ORGANISM: Artificial
<220> FEATURE:
<223> OTHER INFORMATION: primer

<400> SEQUENCE: 4
ggaggatatc tacatgaaaa aagaactg                                      28

<210> SEQ ID NO 5
<211> LENGTH: 19
<212> TYPE: DNA
<213> ORGANISM: Artificial
<220> FEATURE:
<223> OTHER INFORMATION: primer

<400> SEQUENCE: 5
ggcgctggcg gtcgtttgg                                                19

<210> SEQ ID NO 6
<211> LENGTH: 31
<212> TYPE: DNA
<213> ORGANISM: Artificial
<220> FEATURE:
<223> OTHER INFORMATION: primer

<400> SEQUENCE: 6
gcgggatccc atggagatac acctacattg c                                  31

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
acgcagaagc ggtctgataa                                               20

<210> SEQ ID NO 8
<211> LENGTH: 29
<212> TYPE: DNA
<213> ORGANISM: Artificial
<220> FEATURE:
<223> OTHER INFORMATION: primer

<400> SEQUENCE: 8
tctggatcca tgcatggaga tacacctac                                     29

<210> SEQ ID NO 9
<211> LENGTH: 28
<212> TYPE: DNA
```

-continued

```
<213> ORGANISM: Artificial
<220> FEATURE:
<223> OTHER INFORMATION: primer

<400> SEQUENCE: 9
ttgcccataa ccgtagagac cagttgtc                                     28

<210> SEQ ID NO 10
<211> LENGTH: 31
<212> TYPE: DNA
<213> ORGANISM: Artificial
<220> FEATURE:
<223> OTHER INFORMATION: primer

<400> SEQUENCE: 10
actggtctct acggttatgg gcaattaaat g                                 31

<210> SEQ ID NO 11
<211> LENGTH: 31
<212> TYPE: DNA
<213> ORGANISM: Artificial
<220> FEATURE:
<223> OTHER INFORMATION: primer

<400> SEQUENCE: 11
cattctagat cattatggtt tctgagaaca g                                 31
```